(12) United States Patent
Zhou et al.

(10) Patent No.: US 9,976,191 B2
(45) Date of Patent: May 22, 2018

(54) RICE WHOLE GENOME BREEDING CHIP AND APPLICATION THEREOF

(71) Applicants: China National Seed Group Co., Ltd., Beijing (CN); Frontier Laboratories of Systems Crop Design Co., Ltd., Beijing (CN); Huazhong Agricultural University, Wuhan, Hubei (CN); Shenzhen Institute of Molecular Crop Design, Shenzhen, Guangdong (CN)

(72) Inventors: Fasong Zhou, Wuhan (CN); Haodong Chen, Shenzhen (CN); Weibo Xie, Wuhan (CN); Hang He, Shenzhen (CN); Huihui Yu, Wuhan (CN); Xiaoyan Tang, Shenzhen (CN); Jing Li, Wuhan (CN); Junli Zhou, Beijing (CN); Yuqing He, Wuhan (CN); Wei Chen, Beijing (CN); Qifa Zhang, Wuhan (CN); Xingwang Deng, Beijing (CN)

(73) Assignees: China National Seed Group Co., Ltd., Beijing (CN); Frontier Laboratories of Systems Crop Design Co., Ltd., Beijing (CN); Huazhong Agricultural University, Hubei (CN); Shenzhen Institute of Molecular Crop Design, Guangdong (CN)

( * ) Notice: Subject to any disclaimer, the term of this patent is extended or adjusted under 35 U.S.C. 154(b) by 52 days.

(21) Appl. No.: 14/650,762

(22) PCT Filed: Feb. 7, 2013

(86) PCT No.: PCT/CN2013/000131
§ 371 (c)(1),
(2) Date: Jun. 9, 2015

(87) PCT Pub. No.: WO2014/121419
PCT Pub. Date: Aug. 14, 2014

(65) Prior Publication Data
US 2016/0153056 A1    Jun. 2, 2016

(51) Int. Cl.
*C12Q 1/68* (2018.01)
*C07H 21/02* (2006.01)
*C07H 21/04* (2006.01)
*G06F 19/22* (2011.01)

(52) U.S. Cl.
CPC ......... *C12Q 1/6895* (2013.01); *C12Q 1/6837* (2013.01); *G06F 19/22* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 6,582,908 B2 * 6/2003 Fodor .................. B01J 19/0046
435/288.3

FOREIGN PATENT DOCUMENTS

CN    1675373 A    9/2005
CN    102747138 A   10/2012

OTHER PUBLICATIONS

Int'l Search Report dated Nov. 21, 2013 in Int'l Application No. PCT/CN2013/000131.
McCouch et al, "Development of genome-wide SNP assays for rice," Breeding Science, vol. 60, pp. 524-535 (2010).
Ganal et al, "A Large Maize (*Zea mays* L.) SNP Genotyping Array: Development and Germplasm GEnotyping, and Genetic Mapping to Compare with the B73 Reference Genome," PLoS ONE, vol. 6, No. 12, p. e28334 (Dec. 8, 2011).
Chen et al, "Development and application of a set of breeder-friendly SNP markers for genetic analyses and molecular breeding of rice (*Oryza sativa* L.)," Theor. Appl. Genet., published online Jun. 18, 2011.
Jaccoud et al, "Diversity Arrays: a solid state technology for sequence information independent genotyping," Nucleic Acids Research, Vo. 29, No. 4, p. e25 (2001).
Cook et al, "Generic Architecture of Maize Kernel Composition in the Nested Association Mapping and Inbred Association Panels," Plant Physiology, vol. 158, pp. 824-834 (Feb. 2012).
Zhao et al, "Genome-wide association mapping reveals a rich genetic architecture of complex traits in *Oryza sativa*," Nature Communications, vol. 2, No. 467 (Sep. 13, 2011).
Huang et al, "Genome-wide association studies of 14 agronomic traits in rice landraces," Nature Genetics, vol. 42, No. 11, pp. 961-969 (Nov. 2010).
Huang et al, "Genome-wide association study of flowering time and grain yield traits in a worldwide collection of rice germplasm," Nature Genetics, vol. 44, No. 1, pp. 32-41 (Jan. 2012).
McNally et al, "Genomewide SNP variation reveals relationships among landraces and modern varieties of rice," PNAS, vol. 106, No. 30, pp. 12273-12278 (Jul. 28, 2009).
Zhao et al, "Genomic Diversity and Introgression in *O. sativa* Reveal the Impact of Domestication and Breeding on the Rice Genome," PLoS ONE, vol. 5, No. 5, p. e10780 (May 24, 2010).
Thomson et al, "High-throughput single nucleotide polymorphism genotyping for breeding applications in rice using the BeadXpress platform," Mol. Breeding, published online Nov. 20, 2011.

(Continued)

*Primary Examiner* — Carla J Myers
(74) *Attorney, Agent, or Firm* — Panitch Schwarze Belisario & Nadel LLP (57) ABSTRACT

The present invention provides a rice whole genome breeding chip and the application thereof. The rice whole genome breeding chip of the present invention is Rice60K, an SNP chip manufactured based on Infinium technique. Each chip can detect 24 samples simultaneously and contains 58,290 SNP sites. The marker sites have DNA sequences represented by SEQ ID NO.1-58290. The chip can be used in molecular marker fingerprint analysis of the rice variety resources, in genotype identification of the hybrid progeny population, in identification of the variety authenticity, in analysis and screening of the genetic background of the breeding materials, and in association analysis of the agronomic traits, having wide application prospects.

7 Claims, 3 Drawing Sheets

(56) References Cited

OTHER PUBLICATIONS

Borevitz et al, "Large-Scale Identification of Single-Feature Polymorphisms in Complex Genomes," Genome Research, vol. 13, pp. 513-523 (2003).
Miller et al, "RAD market microarrays enable rapid mapping of zebrafish mutations," Genome Biology, vol. 8, No. R105 (Jun. 6, 2007).
Miller et al, "Rapid and cost-effective polymorphism identification and genotyping using restriction site associated DNA (RAD) markers," Genome Research, vol. 17, pp. 240-248, published online Dec. 22, 2006.
Zhou et al, "The Eight Amino-Acid Differences Within Three Leucine-Rich Repeats Between Pi2 and Piz-t Resistance PRoteins Determine the Resistance Specificity to Magnaporthe grisea," MPMI, vol. 19, No. 11, pp. 1216-1228 (2006).

* cited by examiner

RICE WHOLE GENOME BREEDING CHIP AND APPLICATION THEREOF

CROSS-REFERENCE TO RELATED APPLICATION

This application is a Section 371 of International Application No. PCT/CN2013/000131, filed Feb. 7, 2013, which was published in the Chinese language on Aug. 14, 2014, under International Publication No. WO 2014/121419 A1 the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "688936_1US Sequence Listing.txt", creation date of Jun. 4, 2015, and having a size of about 14 MB. The sequence listing submitted via EFS-Web is part of the specification and is herein incorporated by reference in its entirety.

TECHNICAL FIELD

The present invention relates to the fields of genomics, molecular biology, bioinformatics and molecular plant breeding, in particular relates to a rice whole genome breeding chip and the application thereof.

BACKGROUND

In recent years, there have made breakthroughs in DNA sequencing technology, the development of second generation DNA sequencing technology greatly increases the efficiency of genome sequencing and reduces the sequencing time and cost, thus highly facilitating the research on functional genome. In the case of rice, in 2010 the rice molecular biologists in China finished reseqencing of 517 endemic rice variety materials in China by using the second generation sequncing technology, constructed high-density haplotype map (HapMap) of the rice, and conducted association study on 14 important agronomic traits of indica variety by using research method of genome-wide association study (GWAS), thus determined relevant candidate gene locus associated with these agronomic traits and established a set of high throughput genotyping identification methods which are effective and quick, mature and stable, precise and of low cost (Huang et al., Genome-wide association studies of 14 agronomic traits in rice landraces. Nat Genet. 2010, 42: 961-967). Soon afterwards, the number of reseqenced rice varieties increased to 950, more sites related to the regulation of flowering time and grain yield were found by association study (Huang et al., Genome-wide association study of flowering time and grain yield traits in a worldwide collection of rice germplasm. Nat Genet. 2011). Scientists from Huazhong Agricultural University finished the genome-wide resequencing of Minghui 63 and Zhenshan 97 and the cross segregating populations thereof by Illumina sequncing technology, developed a method for high-throughput population genotyping, and constructed an ultra-high-density genetic linkage map of the cross segregating populations of Minghui 63 and Zhenshan 97 comprising 270,000 SNP markers in 210 recombinant inbred lines, which exhibits strong efficacy in QTL mapping analysis (Xie et al., Parent-independent genotyping for constructing an ultrahigh-density linkage map based on population sequencing. Proc Natl Acad Sci USA. 2010, 107: 10578-10583; Yu et al., Gains in QTL detection using an ultra-high density SNP map based on population sequencing relative to traditional RFLP/SSR markers. PLoS One. 2011, 6: e17595). Recently, a cooperative agreement was signed among Chinese Academy of Agricultural Sciences, Shenzhen Huada Gene Research Institute and International Rice Research Institute, a reseqencing project on 3000 rice core germplasm resources collected in the world was initiated, indicating a overall development of rice genome-wide molecular breeding. By the end of 2010, more than 600 rice genes had been successfully cloned, most of which are related to regulation of important agronomic traits including yield, quality, biotic stress resistance and abiotic stress resistance, and nutrition utilization efficiency, etc. Those genes have powerful potential in breeding (Jiang et al., Rice functional genomics research: Progress and implications for crop genetic improvement. Biotechnol Adv. 2011, 30: 1059-1070). Until 2012, over 800 rice genes hayed been cloned. Such research results involved in rice functional genome study provide important foundational data for rice molecular breeding.

Molecular marker technologies are impotent tools for molecular breeding. Conventional molecular marker techniques, such as RFLP (Restriction Fragment Length Polymorphism) and SSR (Simple Sequence Repeat), play an important role in the research on functional genome. However, conventional molecular marker techniques have many limitations such as low throughout, low quantity and complicated operation processes, and they do not meet the needs of large scale breeding for commercial purpose. In order to precisely regulate a target gene, efficiently select genetic background and accurately analyze and identify the varieties for breeding, there is a need for developing and utilizing high throughput molecular marker techniques. At present, there are mainly two platforms for high throughput molecular marker techniques, one is based on the second generation sequencing technology, and the other is based on gene chip technology. Molecular marker techniques based on gene chip mainly include: SNP array (McNally et al., Genomewide SNP variation reveals relationships among landraces and modern varieties of rice. Proc Natl Acad Sci USA. 2009, 106: 12273-12278), SFP (Single Feature Polymorphism) (Borevitz et al., Large-scale identification of single-feature polymorphisms in complex genomes. Genome Res. 2003, 13: 513-523), DArT technology (Diversity Array Technology) (Jaccoud et al., Diversity arrays: a solid state technology for sequence information independent genotyping. Nucleic Acids Res. 2001, 29: E25), RAD (Restriction site Associated DNA) marker (Miller et al., RAD marker microarrays enable rapid mapping of zebrafish mutations. Genome Biol. 2007, 8: R105; Miller et al., Rapid and cost-effective polymorphism identification and genotyping using restriction site associated DNA (RAD) markers. Genome Res. 2007, 17: 240-248), etc. Since SNP sites have the advantages of wide distribution and easy automated detection; among these array-based genotyping technologies, SNP array is most suitable for large scale of commercialized breeding. Currently, Illumina Infinium MaizeSNP50 chip has been used for identification of germplasm resources and association study in maize (Ganal et al., A large maize (Zea mays L.) SNP genotyping array: development and germplasm genotyping, and genetic mapping to compare with the B73 reference genome. PLoS One. 2011, 6: e28334; Cook et al., Genetic architecture of maize kernel composition in the nested association mapping and inbred association panels. Plant physiology. 2011), Affymetrix GeneChip Rice 44K gene chip is used for genetic diversity analysis of rice germplasm resource and genome-wide association study in rice (Zhao et al., Genome-wide association mapping reveals a rich genetic architecture of complex traits in *Oryza sativa*. *Nat Commun.* 2011, 2: 467), and Illumina GoldenGate SNP array with different densities have been used for rice molecular breeding (Zhao et al., Genomic diversity and introgression in *O. sativa* reveal the impact of domestication and breeding on the rice genome. *PLoS One.* 2010, 5: e10780; Chen et al., Development and application of a set of breeder-friendly SNP markers for genetic analyses and molecular breeding of rice (*Oryza sativa* L.). *Theor Appl Genet.* 2011, 123: 869-879; Thomson et al., High-throughput single nucleotide polymorphism genotyping for breeding applications in rice using the BeadXpress platform. *Mol Breeding.* 2011: 1-12).

Infinium SNP chip technology from Illumina Inc. is a genome-wide SNP detection platform, which is currently well developed and widely used, wherein the chips produced by laser confocal optical fiber bead chip technology and unique bead array technology can bear a huge number of beads, thereby coupling to a large number of SNP probes. At present, the human SNP chips produced by Illumina Inc. can accommodate several millions of SNP markers (http://www.illumina.com). When the chips are produced, each SNP probe sequence comprising 20-50 deoxynucleotides is coupled to specific beads, wherein the types of the beads depend on the number of the loaded SNPs, from several thousands to above ten millions. Each type of beads are coded and detected by their particular address sequence and SNP probe sequence. Each type of beads are repeated 15-30 times on average on each chip, so as to ensure the success rate and repeatability for each SNP to be detected. Illumina Infinium SNP chips have been widely used in the genome variation research on species including human and mice, etc. In the case of lacking stable and effective high-density genome-wide breeding chips in rice breeding field, the chip design based on Illumina Infinium platform according to the present invention satisfies the needs for large scale of rice breeding.

DESCRIPTION OF THE INVENTION

One object of the present invention is to provide a rice whole genome breeding chip.

Another object of the present invention is to provide use of the above chip for rice genomic breeding.

The present invention provides a SNP molecular marker combination for rice breeding, which is comprised of 58,290 SNP sites, and the nucleotide sequences thereof are respectively represented by SEQ ID NOs.1-58290.

The present invention provides a rice whole genome breeding chip, named as Rice60K, which comprises 58,290 SNP sites and has nucleotide sequences represented by SEQ ID NOs.1-58290. Most of the 58,290 sequences consist of 101 bases and have a base mutation at position 71.

The present invention has conducted genome-wide sequencing on 211 rice varieties by using Illumina sequencing technology, and 2.5 times of genome coverage has been obtained for each sample. Meanwhile, the inventors have downloaded sequencing data of 520 endemic rice varieties from public database (http://www.ebi.ac.uk/ena/, accession numbers of ERP000106, ERP000235 and ERP000236) and 1 time genome coverage for each of the samples was also obtained (Huang et al., Genome-wide association studies of 14 agronomic traits in rice landraces. *Nat Genet.* 2010, 42: 961-967). The genome sequencing data of 731 rice varieties are achieved in total. The genomes of 731 rice varieties related to the present invention are all obtained by conventional means. The SNPs are identified and screened by the following steps:

1. 3,791,687 SNP sites with high quality are selected from the sequencing data of 731 rice varieties. The SNP sites with high quality should meet the following criteria: SNP sequences are located in specific sequence regions, a SNP site has only two base forms, each of which has a specific proportion, and heterozygous genotypes in the varieties are most likely avoided. In consideration of a certain ratio of error in sequencing, the following conditions are set in the present invention: (1) when the ratios of every kind of base at a site are sorted in descending order, the frequency of the second base is not less than 5%; (2) the number of samples having the third base is less than 10, and the frequency thereof is less than 2.5% (these bases possibly are resulted by errors in sequencing); (3) the frequency of heterozygous genotype is less than 5%; (4) this SNP site is located in non-repeating region.

2. Genotypes of the above-mentioned SNP sites are extracted from 731 rice varieties, and SNP genotypes with missing values are imputed by LD-KNN algorithm (K nearest neighbors). Since the coverage of sequencing was low and a lot of SNP sites were missed, the missing values need to be imputed. It is stipulated in the present invention that the SNP sites after being imputed should meet the following criteria: (1) the ratio of the missing values is less than 50%; (2) at least one linked SNP can be found in the 100 kb region of the rice genome, that is to say, $r^2$ value (r is a correlation coefficient of allele frequency) of LD (linkage disequilibrium) is not less than 0.25. There are 3,679,919 SNP sites which can meet the above criteria.

3. 2,651,614 SNP sites are obtained after the first screening. For each SNP, the 50 bp sequences are extracted at both sides of the SNP sites of Nipponbare (TIGR rice genome anotation version 6.1, http://rice.plantbiology.msu.edu/), Zhenshan 97 and Minghui 63, and a sequence at any side of the SNP sites which meets the following conditions is retained: (1) the sequences of Nipponbare and Zhenshan 97, or the sequences of Nipponbare and Minghui 63 are consistent; (2) the identity of the sequences in any other region of the genome is less than 85%. This step is used for ensuring the specificity and conservatism of the probe sequences on the genome.

4. All the SNPs are divided into 125,062 linkage groups. The rice genome is divided into multiple regions, each comprising 100 kb, with 3,728 regions in total in the genome-wide. $r^2$ value of linkage disequilibrium for any two SNPs in each region is calculated, the SNPs are divided into 125,062 linkage groups by using a greedy algorithm on the basis of $r^2 \geq 0.64$; the SNPs in the same group are considered redundant and referred to as a linkage group. This step is used for ensuring that the selected SNP sites represent the genetic diversity of the varieties as far as possible.

5. 5 SNP sites which have the minor allele frequency (MAF) are selected from each linkage group and the SNP sites with the maximum allele frequency are provided for Infinium iSelect scoring system of Illumina (http://www.illumina.com/) for scoring, the sites with a score less than 0.6 are removed, and 283,451 SNPs are obtained.

6. The present invention defines a comprehensive scoring system, in consideration of Illumina iSelect scoring system scores of the SNP sites, MAF, and the average $r^2$ value of LD for other SNP sites in the same linkage group and the locations in genes. The weighting parameters of all the factors are as follows: (1) the weighting of A/T and G/C change SNP sites (Infinium I) is 0, the weightings of other types of SNP sites (Infinium II) are 20 (since Infinium I needs two kinds of beads to detect one SNP, while Infinium II only needs one kind of bead, and it is best to choose Infinium II in order to deploy SNP sites as many as possible on a chip); (2) the weighting of Illumina iSelect scoring system is 10 (the values of scoring reflect the success rate for probe designing); (3) the weighting of minor allele frequency (MAF) is 40 (the higher the MAF is, the bigger the possibility of polymorphism between any two varieties is); (4) the weighting of LD average $r^2$ value is 5 ($r^2$ values reflect the degree of linkage between SNPs); (5) depending on the location of a SNP in the gene region, the weightings of intergenic, intron, promoter, 5'-end non-coding region (5'-UTR) and 3'-end non-coding region (3'-UTR) are 1, 1.5, 2, 2 and 2.5 (scoring is based on degree of effect of regions with different gene structures on gene function) respectively, and the weightings of synonymous mutation, nonsynonymous muation and large effect mutation (eg. non-sense mutations) occurring in the coding region are 2, 5 and 10 (base mutation in coding region is directly related to function) respectively.

4,646 SNP/INDEL sites with high quality on SNP chip of Rice6K rice (Chinese invention patent No. 201210055775.X) and 1000 SNP sites on the cloned important rice function genes are directly used for synthesizing the probes for Rice60K breeding chip; and 58,290 SNP sites are obtained in total, the nucleotide sequences of which are respectively represented by SEQ ID NOs.1-58,290. Each of the above 58290 sequences consists of 101 bases and has a base mutation at position 71. It can be seen from the sequence listing that each of the 58,290 sequences has a SNP site at position 71.

After identifying and screening in accordance with the above steps, finally 58,290 tagSNP sites are obtained in total. Since 60,000 kinds of beads are needed according to requirements for designing of Illumina Infinium iSelect HD, the chip is named Rice60K. All the 58,290 tag SNP sites correspond to the Nos. 1-58290 DNA sequences in the sequence listing. These tag sequences are provided for Illumina for designing Infinium SNP chip.

The Rice60K gene chip in the present invention is an optical fiber bead chip made by Infinium SNP chip technology (U.S. Pat. No. 6,429,027) and can detect 24 samples simultaneously on a chip.

Further, the present invention provides a method for preparing the above gene chip, comprising the steps of: (1) obtaining genome sequences of plenty of rice varieties by resequencing, and, and analyzing and identifying SNP sites using Nipponbare genome as reference sequence in combination with resequencing data of other rice varieties in the public database, and selecting representative SNP markers to directly synthesize probe; the nucleotide sequences of the SNP markers are respectively represented by SEQ ID NOs.1-58,290; (2) preparing SNP chips using Infinium chip manufacture technology; (3) testing the accuracy and the application efficiency of the chips.

Particularly, the present invention provides the use of a Rice60K rice whole genome breeding chip in detecting rice DNA samples, comprising the steps of:

(1) extracting rice genome DNA: genome DNA is extracted from rice tissues including seeds or leaves in accordance with the requirement for detection. For extracting DNA from young rice leaves, it is preferable to use Promega or Qiagen plant genome preparation kit, and for extracting DNA from endosperms of rice seeds, it is preferable to use the complicated plant genome preparation kit from Beijing ComWin Biotech.

(2) detecting the quality of the DNA samples: electrophoresis detection is carried out using 1% agarose gel and the electrophoresis results are evaluated by gel imaging system to ensure that the genome DNA has a good integrity and the size of the genome DNA fragments is more than 10 kb in length. The concentration of genome DNA is measured by ultra-violet spectrophotometer, and the genome DNA is diluted to a working concentration of 10-50 ng/µl.

(3) detecting the gene chips: the gene chips are detected according to Infinium assay standard protocol, and scanned using Illumina HiScan chip scanner.

(4) analyzing the data: the scanning results from Illumina HiScan are analyzed to calling genotypes by using GenomeStudio software, and programmed by using R language to obtain a comparing result of genotypes.

Further, the present invention provides the use of the above Rice60K rice whole genome breeding chip in fingerprint analysis of rice germplasm resource.

The present invention provides the use of the above Rice60K rice whole genome breeding chip in identification of genotypes of rice hybrid progeny.

The present invention provides the use of the above Rice60K rice whole genome breeding chip in identification of rice varieties.

The present invention provides the use of the above Rice60K rice whole genome breeding chip in detecting rice breeding materials.

The present invention provides the use of the above Rice60K rice whole genome breeding chip in rice genome-wide association study.

As compared with other molecular marker detection systems, the present invention has the following advantages and effects:

(1) as compared with traditional molecular markers such as SSR, the present invention has advantages including high throughout, low cost for a single marker data, etc. It is difficult to develop 200 polymorphism SSR markers in rice genomes by traditional method. On the contrary, Rice60K breeding chip is used for detecting any two of the varieties, any two of the indica varieties, any two of the *japonica* varieties, or one indica variety and one *japonica* variety, and about 14,000, 10,000, 8,000 and 19,000 polymorphism SNP sites with high quality can be obtained on average, respectively.

(2) as compared with other genotyping systems based on gene chip platform, the present invention has advantages including good repeatability, high throughout, and simple data analysis, etc. The technological repeatability of detecting rice samples by using Rice60K breeding chip can be above 99.99%, and it is difficult for the other prior genotyping platforms to reach such a percentage.

(3) as compared with the genotyping systems based on the second generation sequencing platform, the present invention has advantages including simple data analysis and comparability between data from different laboratories. With the development of sequencing technology, the cost of sequencing is becoming lower, and the sequencing throughout is increasing. However, the requirement for sequencing data analysis is getting higher and higher, and professional analysis software and bioinformatics experts are also needed for the analysis, while the data analysis of Rice60K breeding chip platform is relatively very simple; since sequencing itself is random and it is difficult to directly compare the different batches of sequencing data with low coverage, and the cost of deep sequencing is still high; since most of the markers on the Rice60K breeding chip are fixed, it is convenient to compare different batches of detection data.

However, a great number of sequencing data generated by the second generation sequencing system provides important foundational data for designing a gene chip. Therefore, the second generation sequencing and the gene chip systems are complementary to each other.

(4) as compared with the previous patented Rice6K chip (Chinese patent No. 201210055775.X), Rice60K according to the present invention has a wide range of applicability. 1) the markers selected on the Rice60K chip involves more and wider range of rice varieties. The markers on the Rice6K chip were mainly selected from the sequencing data of over 520 endemic rice varieties, while the markers on the Rice60K chip come from over 730 rice varieties, including both the previous endemic rice varieties in China and the ones from rice mini-core collection of germplasm resources from all over the world, as well as the parents of rice hybrids which are widely planted in China. 2) the genetic diversity represented by the markers on the Rice60K chip is more abundant. Generally speaking, the difference between *japonica* varieties is less than the difference between indica varieties, and the latter is then less than the difference between subspecies of *japonica* and indica, the design of Rice6K chip is mainly focused on the difference between subspecies of *japonica* and indica, the proportion of polymorphism SNPs is low within subspecies, especially between *japonica* varieties. For the markers on the Rice60K breeding chip, it is desirable to select the polymorphic sites between the varieties within rice subspecies, especially between *japonica* varieties, such that the Rice60K breeding chip can be used well not only for detecting cross population between rice subspecies, but also for detecting cross population within rice subspecies (see Example 6); 3) Rice60K chip includes a large number of sites related to function genes. Firstly, the markers on the Rice60K chip are apt to select the SNP sites in gene coding region, especially the sites affecting the change of gene function, such as non-sense mutations, while this was not taken into account when the Rice6K chip was designed; secondly, the Rice60K chip includes about 1000 SNP sites in the cloned important rice genes, while the Rice6K chip has few functional gene sites. 4) the Rice60K breeding chip comprises all the SNP sites with high quality on Rice6K chip, Rice60K chip thus has more markers and the distribution density of the markers on the genome is higher.

BRIEF DESCRIPTION OF FIGURES

FIG. 2 is a genotype clustering diagram of 195 rice homozygous varieties. The distance is the ratio of the number of polymorphic sites between two varieties to the number of total sites, and the genotypes of 195 rice samples were clustered using hierarchical cluster analysis method. The ids of the samples are Nos. 1-195, respectively. The indica group is at the left side, the *japonica* group is at the right side, and the intermediate types are in the middle.

FIG. 4 are genotyping maps of representative lines from 4 segregating populations. Each line on the chromosome indicates one SNP site, grey parts indicate female parent (Zhenshan 97) homozygous genotype, and black parts indicate male parent homozygous genotype. Panel A is a map of a line of Zhenshan 97/Minghui 63 RIL population; panel B is a map of a line of Zhenshan 97/XiZang 2; panel C is a map of a introgression line of introducing Nipponbare into Zhenshan 97; panel D is a map of a introgression line of introducing ordinary wild rice (IRGC-105491) into Zhenshan 97.

SPECIFIC MODE FOR CARRYING OUT THE PRESENT INVENTION

Examples are described below to illustrate the present invention but not intended to limit the scope thereof. The alterations or modifications of the methods, steps or conditions of the present invention made without departing from the spirit and essence thereof will be in the scope of the present invention. Unless otherwise indicated, the technical means used in the following examples are conventional means well known to a person skilled in the art.

Example 1

Preparation Method of the Rice60K Rice Whole Genome Breeding Chip

In the present invention, genome-wide sequences for 211 rice varieties were sequenced by Illumina sequencing technology, and 2.5 times genome coverage data was obtained for each sample, see Table 1. Meanwhile, in the present invention, sequencing data of 520 endemic rice varieties were also downloaded from public database (http://www.ebi.ac.uk/ena/, accession numbers of ERP000106, ERP000235 and ERP000236), and 1 time genome coverage data was obtained for each of the samples (Huang et al., Genome-wide association studies of 14 agronomic traits in rice landraces. *Nat Genet.* 2010, 42: 961-967). In total, the genome sequencing data of 731 rice varieties were obtained. The SNPs were identified and screened according to the following steps:

TABLE 1

Names of 211 rice varieties

| No. | Name |
|---|---|
| 1 | Sadu-cho |
| 2 | Dom Sufid |
| 3 | Gerdeh |
| 4 | Lijiangxintuanheigu |
| 5 | AZUCENA |
| 6 | San huang zhan 2-1 |
| 7 | San huang zhan 2-2 |
| 8 | Swarna |
| 9 | MOROBEREKAN |
| 10 | CYPRESS |
| 11 | WH11 |
| 12 | Tainong 67 |
| 13 | N 22 |
| 14 | M202 |
| 15 | Dular |
| 16 | Laoguangtou 83 |
| 17 | Annong wanggeng B-1 |
| 18 | Annong wanggeng B-2 |
| 19 | Aijiaonante |
| 20 | Guangluai 4 |
| 21 | Xiangaizao 10 |
| 22 | Jinnante B |
| 23 | Funingzipi |
| 24 | Zhenshan 97 B |
| 25 | Qingsiai 16B |
| 26 | Weiguo |
| 27 | Dianrui 409B |
| 28 | Liaogeng 287 |
| 29 | Huhui 628 |
| 30 | 88B-1 |
| 31 | 88B-2 |
| 32 | Longhuamaohu |
| 33 | Lucaihao |
| 34 | Zhonglouyihao-1 |
| 35 | Yelicanghua |
| 36 | Shufeng 101 |
| 37 | Chengduai 3 |
| 38 | Sankecun |
| 39 | Gongju 73 |
| 40 | Jiabala |
| 41 | Taishannuo |
| 42 | Guichao 2 |
| 43 | Huke 3 |
| 44 | Teqingxuanhui |
| 45 | Huangsiguizhan |
| 46 | Xiangwanxian 3 |
| 47 | Hanmadao-2 |
| 48 | Zaoshunonghu 6 |
| 49 | Jinyou 1 |
| 50 | Chengnongshuijing |
| 51 | Pei C122 |
| 52 | Guihuahuang |
| 53 | Momi |
| 54 | Xiushui 115 |
| 55 | Sanbaili |
| 56 | Jindao 1 |
| 57 | Dandongludao |
| 58 | Liusha 1 |
| 59 | Bawangbian 1 |
| 60 | Dongtingwanxian |
| 61 | Yangdao 2 |
| 62 | WH62 |
| 63 | Geng 87-304 |
| 64 | Sugeng 2 |
| 65 | Hongwan 1 |
| 66 | Liushizao |
| 67 | Muxiqiu |
| 68 | Taizhongxianxuan 2 |
| 69 | Dangyu 5 |
| 70 | Youmangzaogeng |
| 71 | Laohuzhong |
| 72 | Nantehao |
| 73 | Esiniu |
| 74 | Cunsanli |
| 75 | Huangkezaonian |
| 76 | Benbanggu-1 |

TABLE 1-continued

Names of 211 rice varieties

| No. | Name |
|---|---|
| 77 | Benbanggu-2 |
| 78 | Qitoubaigu |
| 79 | Muguanuo-1 |
| 80 | Hanmadao-1 |
| 81 | Heidu 4 |
| 82 | Gaoyangdiandao |
| 83 | Chikenuo |
| 84 | Haobuka |
| 85 | Shanjiugu |
| 86 | Fanhaopi |
| 87 | Lixingeng |
| 88 | Nangaogu-2 |
| 89 | Tieganwu |
| 90 | Sanlicun |
| 91 | Meihuanuo-1 |
| 92 | Meihuanuo-2 |
| 93 | Xiangnuo-2 |
| 94 | Menjiagao 1 |
| 95 | Xiaohonggu |
| 96 | Jinxibai-1 |
| 97 | Jinbaoyin |
| 98 | Hongainuo |
| 99 | WH099 |
| 100 | WH100 |
| 101 | Babaili |
| 102 | Qiyuexian |
| 103 | Yuyannuo-1 |
| 104 | Mamagu-1 |
| 105 | WH105 |
| 106 | Hongkezhenuo |
| 107 | Mowanggunei-2 |
| 108 | Mamagu-2 |
| 109 | WH109 |
| 110 | Xianggu |
| 111 | Ximaxian |
| 112 | Jinnante 43B |
| 113 | Xiangzaoxian 7 |
| 114 | 80B |
| 115 | WH115 |
| 116 | Liming B |
| 117 | Jiangnongzao 1 |
| 118 | Gu 154 |
| 119 | Ninghui 21 |
| 120 | Shuiyuan300li |
| 121 | Xiangai B |
| 122 | Aituogu 151 |
| 123 | Taidongludao |
| 124 | Menjiading 2 |
| 125 | Jiefangxian |
| 126 | Hongqi 5 |
| 127 | Baikehualuo |
| 128 | Liuyenian |
| 129 | Aihechi |
| 130 | Xiangnuo-1 |
| 131 | Xuanenchangtan |
| 132 | Jinzhinuo |
| 133 | Muguanuo-2 |
| 134 | Wizidui |
| 135 | Xibainian |
| 136 | Zegu |
| 137 | Cungunuo |
| 138 | Lengshuigu 2 |
| 139 | WH139 |
| 140 | Wujuhonggu |
| 141 | Nangaogu-1 |
| 142 | Mowanggunei-1 |
| 143 | Qitougu |
| 144 | Huangpinuo |
| 145 | Zhenshan 97B-2 |
| 146 | Nipponbare |
| 147 | Minghui 63 |
| 148 | 93-11 |
| 149 | Zhonghua 11 |
| 150 | Balila |
| 151 | Nanjing 11 |
| 152 | 02428 |

TABLE 1-continued

Names of 211 rice varieties

| No. | Name |
|---|---|
| 153 | IRAT109 |
| 154 | Heigeng 2 |
| 155 | Erjiunan 1 |
| 156 | Chaoyang 1 B |
| 157 | L301B |
| 158 | Guangluai 15 |
| 159 | Zhuzhen B |
| 160 | Baoxie-7B |
| 161 | G Zhenshan 97 B |
| 162 | Nanxiongzaoyou |
| 163 | Zaoshuxianghei |
| 164 | IR661-1 |
| 165 | Nanjiang 11-2 |
| 166 | Gui 630 |
| 167 | 76-1 |
| 168 | Xugunuo |
| 169 | Taizhongzailai 1 |
| 170 | Xiangwanxian |
| 171 | Xinguo |
| 172 | Zhonghua 8 |
| 173 | Aimakang |
| 174 | JWR221 |
| 175 | Zhenxian 232 |
| 176 | Chenwan 3 |
| 177 | Maguzi |
| 178 | Aimi |
| 179 | Haobayong 1 |
| 180 | Wanlixian |
| 181 | Feidongtangdao |
| 182 | Hengxianliangchun |
| 183 | Leihuozhan |
| 184 | Baikeaohe |
| 185 | Haomake (K) |
| 186 | Sanbangqishiluo |
| 187 | Niankenuo |
| 188 | Yangkenuo |
| 189 | Putaohuang |
| 190 | Xiangdao |
| 191 | Younian |
| 192 | Wukezhan |
| 193 | Zhongnong 4 |
| 194 | Minbeiwanxian |
| 195 | Hongmisandan |
| 196 | Yuyannuo-2 |
| 197 | Maweinian |
| 198 | Zinuo |
| 199 | Beizinuo |
| 200 | Biwusheng |
| 201 | Yizhixiang |
| 202 | Xiaobaimi |
| 203 | Zaoxian |
| 204 | HD9802S |
| 205 | Y58S |
| 206 | Kongyu 131 |
| 207 | Guangzhan 63-4S |
| 208 | B5 |
| 209 | Daohuaxiang |
| 210 | Yuexiangzhan |
| 211 | X Zhenshan 97 B |

1. 3,791,687 SNP sites with high quality were identified from the sequencing data of 731 rice varieties. The SNP sites with high quality should meet the following conditions: (1) when the ratios of every kind of base at a site are sorted in descending order, the frequency of the second base is not less than 5%; (2) the number of samples having the third base is less than 10, and the frequency thereof is less than 2.5%; (3) the frequency of heterozygous genotype is less than 5%; (4) this SNP site is located in non-repeating region.

2. Genotypes of the above-mentioned SNP sites were extracted from 731 rice varieties, and the SNP genotypes with missing values were imputed by LD-KNN algorithm (K nearest neighbors). 3,679,919 SNP sites with missing values can be imputed by this method. Afterwards, these sites should meet the following conditions: (1) the ratio of the missing values is less than 50%; (2) at least one linked SNP can be found in the 100 kb region of the rice genome, that is to say, $r^2$ value of linkage disequilibrium (LD) is not less than 0.25, wherein r is a correlation coefficient of allele frequency.

3. 2,651,614 SNP sites were obtained after the first screen. For each SNP, 50 bp sequences were extracted at both sides of the SNP sites of Nipponbare, Zhenshan 97 and Minghui 63, and a sequence at any one side of the SNP sites which meets the following conditions was retained: (1) the sequences of Nipponbare and Zhenshan 97, or the sequences of Nipponbare and Minghui 63 are consistent; (2) the identity of the sequences in any other region of the genome is less than 85%.

4. All the SNPs were divided into 125,062 linkage groups. The rice genome was divided into bins (small region), each comprising 100 kb, with 3,728 bins in total in the genome-wide. $r^2$ value of linkage disequilibrium for any two SNPs in each bin was calculated, the SNPs were divided by using greedy algorithm on the basis of $r^2 \geq 0.64$; the SNPs in the same group were considered redundant.

5. 5 SNP sites which had the minor allele frequency (MAF) were selected from each linkage group and SNP sites with the maximum allele frequency were provided for Illumina Infinium iSelect scoring system (http://www.illumina.com/) for scoring, and the sites with a score less than 0.6 were removed.

6. The present invention defines a comprehensive scoring system, in consideration of Illumina iSelect scoring system scores of the SNP sites, MAF, and the average $r^2$ value of LD for other SNP sites in the same linkage group and the locations in genes. The weighting parameters of all the factors were determined experientially and they are as follows: (1) the weighting of A/T and G/C change SNP sites (Infinium I) is 0, the weightings of other types of SNP sites (Infinium II) are 20; (2) the weighting of Illumina iSelect scoring system is 10; (3) the weighting of minor allele frequency (MAF) is 40; 4) the weighting of LD average $r^2$ value is 5; (5) depending on the location of a SNP in the gene region, the weightings of intergenic, intron, promoter, 5'-end non-coding region (5'-UTR) and 3'-end non-coding region (3'-UTR) are 1, 1.5, 2, 2 and 2.5, respectively, and the weightings of synonymous mutation, non-synonymous mutation and large effect mutation (eg. non-sense mutations) occurring in the coding region are 2, 5 and 10, respectively.

4,646 SNP/INDEL sites with high quality on SNP chip of Rice6K rice (Chinese invention patent, 201210055775.X) and 1000 SNP sites on the cloned important rice function genes were directly used for synthesizing the probes for Rice60K breeding chip.

Figure 1:
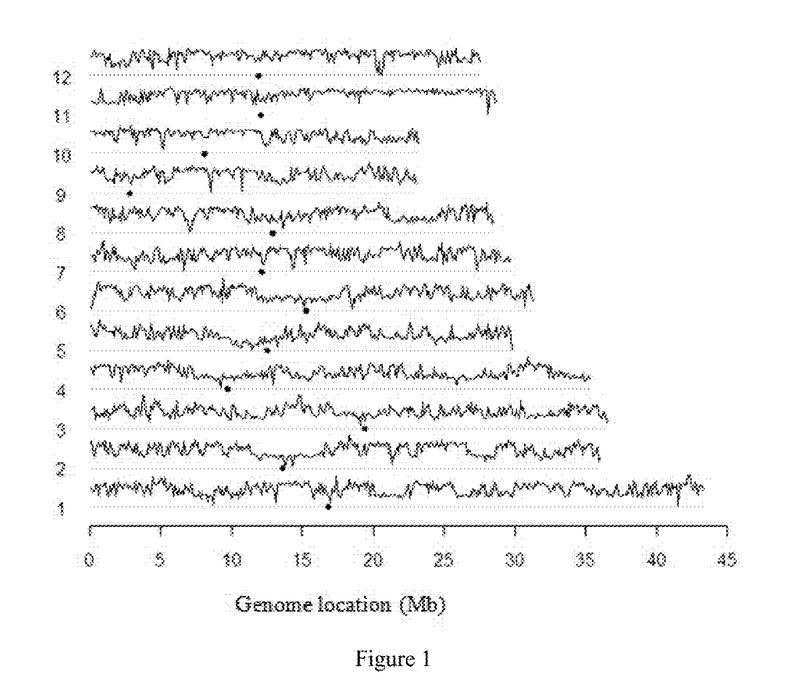
FIG. 1 is schematic diagram showing the distribution of 51,599 SNP markers on rice genome on the Rice60K rice whole genome breeding chip. Reference genome is Nipponbare (TIGR rice genome annotation version 6.1). The curve on each chromosome is the ligature of the number of SNP sites in each 100-kb region, the maximum is set for 25 SNPs/100-kb, and the dot on each chromosome indicates the position of centromere.

After identifying and screening in accordance with the above steps, finally 58,290 tag SNP sites (tagSNP) were obtained in total, and 60,000 kinds of beads are needed according to the requirements for designing of Illumina Infinium iSelect HD. All the 58,290 tag SNP sites correspond to the Nos. 1-58,290 DNA sequences in the sequence listing. These tag sequences were provided for Illumina for designing Infinium SNP chip. 51,599 effective sites meeting the requirements for detection were obtained by chip preparation, and the distribution of these sites on genome-wide was shown in FIG. 1.

Example 2

Application of Rice60K Rice Whole Genome Breeding Chip in Detecting Rice DNA Samples Extraction of rice genome DNA: genome DNA was extracted from rice tissues including seeds or leaves in accordance with the requirement for detection. For extracting DNA from young rice leaves, it is preferable to use Promega plant genome preparation kit (Wizard Magnetic 96 DNA Plant System Kit, Item No. FF3760 or FF3761, Beijing Promega biological technology Co. Ltd.), and for extracting DNA from endosperms of rice seeds, it is preferable to use the complicated plant genome preparation kit from Beijing ComWin Biotech (SurePlant DNA Kit, Item No. CW0555, Beijing ComWin Biotech Co. Ltd.).

Detection of the quality of the DNA samples: electrophoresis detection was carried out using 1-1.5% (W/W) agarose gel, and the electrophoresis results were evaluated by gel imaging system (Gel Doc XR System, Bio-Rad Co., US) to ensure that the genome DNA has a good integrity and the size of the genome DNA fragments is more than 10 kb in length. The concentration of genome DNA was measured by micro-volume ultra-violet spectrophotometer (Q5000, Quawell Co., US) or similar nucleic acid and protein detector, and the genome DNA was adjusted to a working concentration of 10-50 ng/µl.

Detection of the gene chips: the gene chips were detected according to Infinium assay standard protocol (Infinium HD Assay Ultra Protocol Guide, http://www.illumina.com/), and scanned using Illumina HiScan chip scanner (HiScan, Illumina Co., US).

Analysis of the data: the scanning results from Illumina HiScan were analyzed to calling genotypes by GenomeStudio software (http://www.illumina.com/), and programmed by using R language to obtain a comparing result of the genotypes.

Example 3

Figure 2:
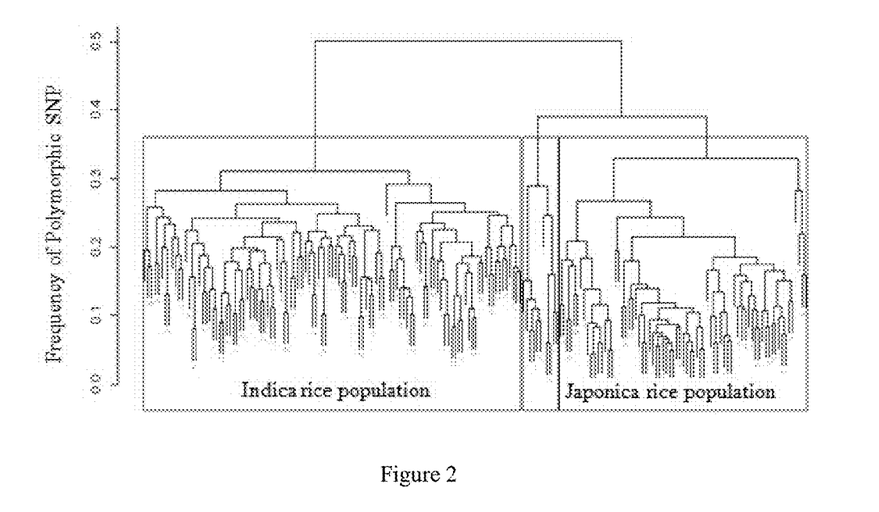
Figure 3:
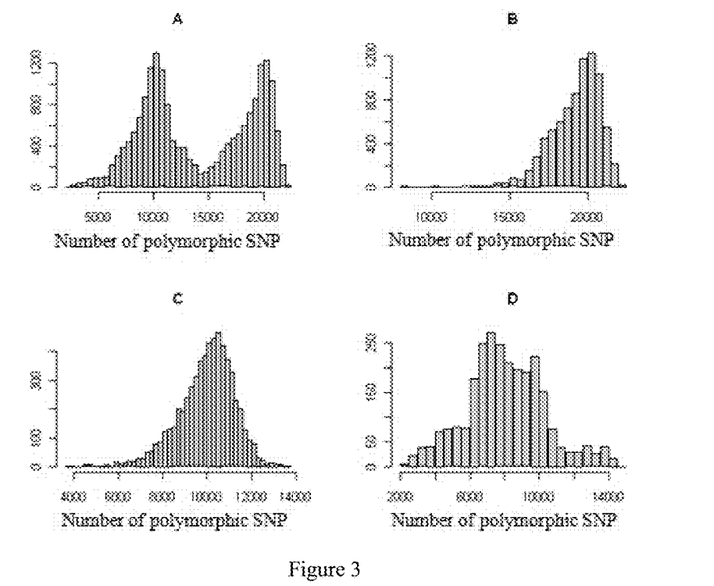
FIG. 3 are schematic diagrams showing the distributions of polymorphism SNPs among different types of rice obtained by Rice60K chip detection. The panels show the histograms of polymorphism SNP sites distribution between any two varieties. Panel A is a diagram showing the number distribution between random two varieties; panel B is a diagram showing the number distribution between two subspecies of indica and *japonica*; panel C is a diagram showing the number distribution between indica varieties; panel D is a diagram showing the number distribution between *japonica* varieties.

Application of Rice60K Rice Whole Genome Breeding Chip in Gene Fingerprint Analysis for Rice Germplasm Resource With reference to the method of Example 2, 270 varieties from the mini-core collection of rice germplasm resource (No. WCR001-270) from China National Seed Group CO., LTD., were detected by Rice60K breeding chip in the present invention, and among them, 195 representative varieties of self-pollinating homozygote were selected for analysis. The genotypes of the 195 representative varieties were detected by Rice60K breeding chip, and 195 varieties may be divided into three groups by cluster analysis: indica group, *japonica* group, and intermediate group (see FIG. 2), which was consistent with the classification results based on phenotype. Between any two of the varieties, between indica and *japonica*, between any two of the indica varieties, and any two of the *japonica* varieties, the average number of polymorphism SNP sites are 14,000, 19,000, 10,000 and 8,000 respectively (see FIG. 3). These results show that, SNP sites of the Rice60K breeding chip have applicability in a wide range, and they can even be used to detect and well distinguish *japonica* varieties which have small differences. Therefore, Rice60K breeding chip is particularly suitable for establishing gene fingerprint database for rice varieties, helping breeding scientists search and compare the genetic relationships between varieties and select breeding materials.

Example 4

Figure 4:
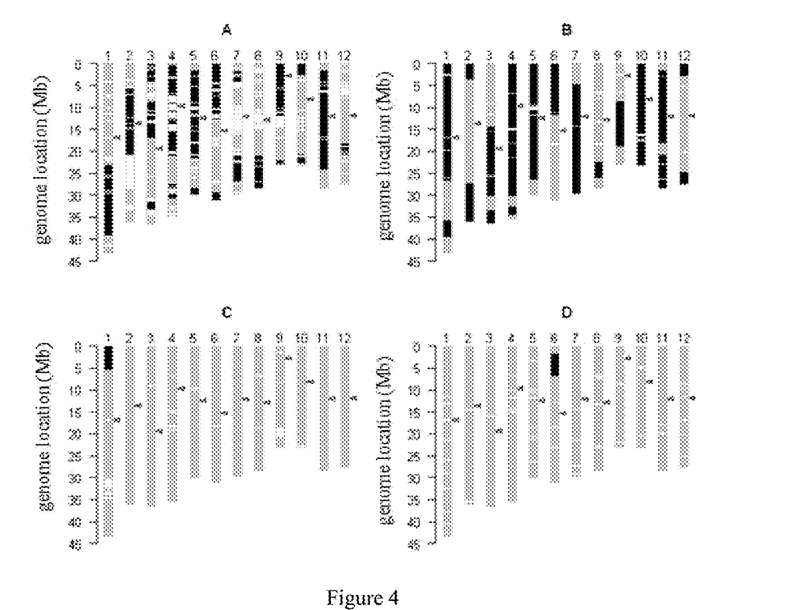

Application of Rice60K Rice Whole Genome Breeding Chip in Genotyping Rice Segregating Populations The genotypes of the following populations were detected by Rice60K chip in the present invention: 2 recombinant inbred line (RIL) populations, i.e., Zhenshan 97/Minghui 63 RIL population, Zhenshan 97/Zizang 2 RIL population, and 2 chromosome segment substitution line (CSSL) populations, i.e., a introgression line of Zhenshan 97, into which Nipponbare was introduced, and a introgression line of Zhenshan 97. into which an ordinary wild rice (IRGC-105491) was introduced (refer to the method of Example 2); the genotypes of one representative line from each of the populations are shown in FIG. 4. FIG. 4 shows that, Rice60K chip has very good effect on genotyping for different populations with advantages of high density of markers and clear recombinant breakpoints. Rice60K chip can detect the double crossover region which can not be detected by the traditional molecular markers such as SSR, furthermore, it has more accurate and reliable detection results due to the high density of markers. The results demonstrate that, as a molecular marker detection system, Rice60K rice whole genome breeding chip can genotype rice cross segregating populations well.

Example 5

Figure 5:
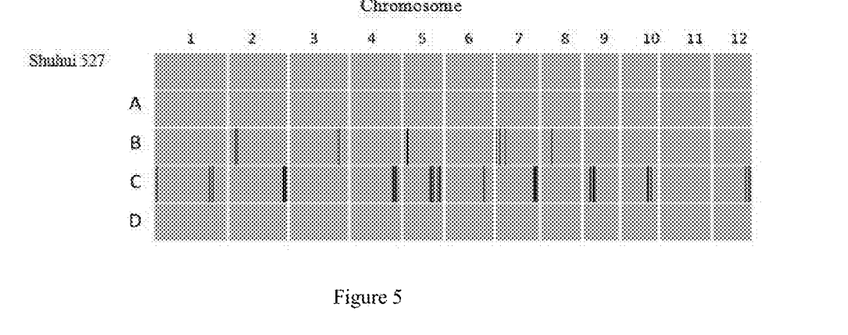
FIG. 5 is schematic diagram showing SNP genotyping comparison of five Shuhui 527 samples with different origins. Grey lines indicate SNP sites consistent with the standard Shuhui 527 sample, and black lines indicate SNP sites which are not consistent with the standard sample.

Application of Rice60K Rice Whole Genome Breeding Chip in Identifying Rice Varieties Four kinds of seeds (A, B, C, D) marked as Shuhui 527 were collected from the market, they cannot be distinguished from each other in phenotype; and standard Shuhui 527 material was collected from Sichuan Agricultural University, who is the breeder of Shuhui 527, and was used as a control. The 5 samples were detected by Rice60K rice whole genome breeding chip (Refer to the method of Example 2). With respect to the genotype, the 4 kinds of seeds of Shuhui 527 from the market and were compared with the control based on the detection results. Shuhui 527, which has been bred for many years, can be considered as homozygous parent. After removing the heterozygous sites and the sites with GenTrain Score less than 0.6, 38,310 SNP sites with high quality were obtained. Genotype comparison of the 5 samples is shown in FIG. 5. It can be seen from the results that, A and D are consistent with Shuhui 527 from the breeder, while 4% genotypes of B and C are distinctive from that of Shuhui 527, and it can be concluded that B and C are not Shuhui 527 varieties. These results demonstrate that, Rice60K gene chip can be advantageously used in identifying the authenticity of rice varieties, and the identification results are precise and reliable.

Example 6

Figure 6:
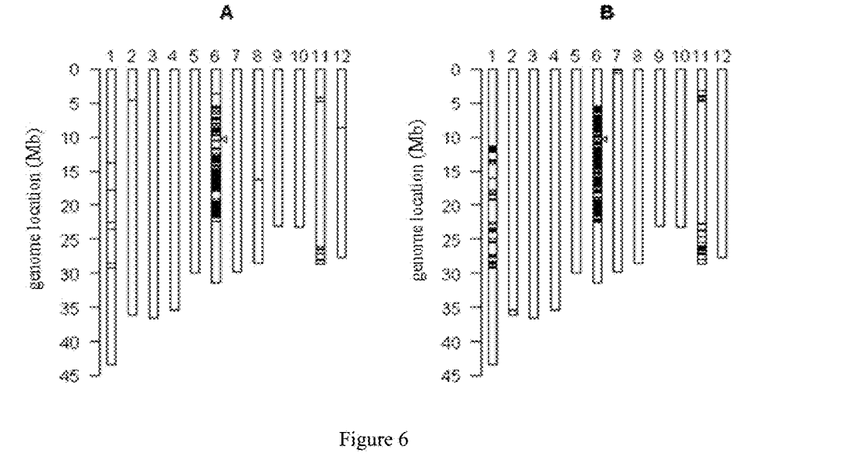
FIG. 6 are schematic diagrams showing the genetic background detection results of the improved line A8 from Kongyu 131 by Rice6K and Rice60K chips, respectively. For the chromosome regions without line in the diagrams, the background is recovered consistent with genotype of recipient parent Kongyu 131, and the black lines are heterozygous genotype SNP sites. The triangle arrows indicate the location of target gene Pit. Panel 6A is a diagram showing the detection result of Rice6K; and panel 6B is a diagram showing the detection result of Rice60K.

Application of Rice60K Rice Whole Genome Breeding Chip in Genetic Background Analysis of Rice Breeding Materials In order to test the application effect of Rice60K breeding chip in genetic background analysis of rice breeding materials, the rice varieties Kongyu 131 and improved line A8 thereof were detected in the present invention (Refer to the method of Example 2). A8 is a single plant of the BC4F1 generation, the target gene is rice blast resistance gene Pi2 (Zhou et al., The eight amino-acid differences within three leucine-rich repeats between Pi2 and Piz-t resistance proteins determine the resistance specificity to *Magnaporthe grisea*. Mol Plant Microbe Interact. 2006, 19: 1216-1228). As compared with the recipient parent Kongyu 131, the genetic background of A8 is shown in FIG. 6. It can be seen from FIG. 6 that, the plant has not only introduced Pi2 gene and the big fragment adjacent to Pi2 gene on chromosome 6, but also has combined at least 3 donor fragments on chromosomes 1 and 12. Both Rice6K chip and Rice60K chip can effectively detect Pi2 gene and the big fragments adjacent to Pi2 gene. However, the effect of Rice60K chip is significantly better than that of Rice6K chip when detecting the other background. The recipient parent Kongyu 131 is *japonica*, while the donor parent Pi2 gene and the adjacent regions are indica fragments, and the other locations are in *japonica* background. Since Rice6K chip is mainly designed for indica and *japonica* hybrids, when it is used for detecting the hybrids between *japonica*, the polymorphism is low; while Rice60K breeding chip can effectively detect the hybrids between *japonica* since it has greatly increased marker density and the polymorphism between *japonica* varieties was taken into account when designing the probe. It thus can be seen that Rice60K rice whole genome breeding chip has good effect in analyzing genetic background of breeding materials.

Example 7

Figure 7:
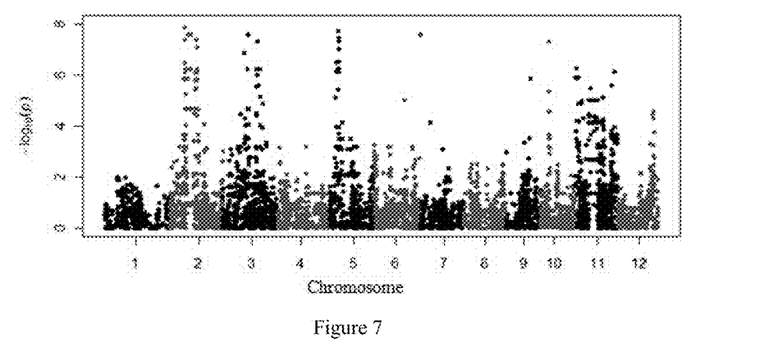
FIG. 7 is a Manhattan plot showing the association study for grain wide trait of Huanghuazhan lineage.

Application of Rice60K Rice Whole Genome Breeding Chip in Rice Association Study Huanghuazhan and its lineage varieties, a total number of which is 21, were collected to investigate an important agronomic trait, viz. grain width, and to analyze the relationship between genome change and gain width of Huanghuazhan and its lineage varieties. Quality control was given to the genotyping results from Rice60K chip (Refer to the method of Example 2), and genotyping information with high quality was obtained by screening. SNP sites of the samples with GenTrain Score less than 6 were removed, since these sites have poor reliability and can not be used for data analysis. The sites with a missing genotype rate less than 0.2 in these 21 varieties were further removed, since the missing sites can not be effectively used for further analysis of the data due to data loss, and finally 42,387 SNP sites were obtained. Association study was conducted on the basis of the grain wide traits of the collected rice seeds and the resulting SNP sites, obtaining a Manhattan plot shown in FIG. 7. Analysis shows that 5 sites on the chromosome have remarkable relevance, and mapping shows that Region 2 of the chromosome contains the known GW2 gene, Region 3 of the chromosome contains the known GS3 gene, and Region 5 of the chromosome contains the known GWS gene, while the QTLs on chromosome 6 and chromosome 10 are new potential regulation sites. Therefore, identifying genotype by using Rice60K SNP chip can obtain a more precise result of association study with high density of genotyping data.

The present invention has been illustrated here in detail by general description and specific embodiments, however, on the basis of the disclosure of invention it is obvious to a person skilled in the art that some alterations or modifications can be made. Therefore, the alterations or modifications made without departing from the spirit of the present invention will be in the scope of the present invention.

INDUSTRIAL APPLICATION

The chip according to the present invention is a SNP chip manufactured by Infinium SNP chip technology, which comprises 58,290 SNP sites and can be used to analyze molecular marker fingerprint of rice variety resources, identity genotype of progeny of cross populations, identity authenticity of varieties, analyze and screen genetic background of breeding materials, and analyze the association of agronomic traits. The chip thus has important economic values and prospects of application.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09976191B2). An electronic copy of the "Sequence Listing" will also be available from the USPTO upon request and payment of the fee set forth in 37 CFR 1.19(b)(3).

What is claimed is:

1. A collection of marker nucleic acids for rice genotyping, wherein the collection of marker nucleic acids consists of 58,290 nucleotide sequences, wherein each of the nucleotide sequences is coupled to a bead and comprises a SNP and the nucleotide sequences thereof consist of SEQ ID NOs.1-58,290.

2. A rice whole genome breeding chip, wherein the rice whole genome breeding chip comprises 58,290 nucleotide sequences, wherein each of the nucleotide sequences is coupled to a bead and comprises a SNP and the nucleotide sequences consist of SEQ ID NOs.1-58,290.

3. A method comprising using the rice whole genome breeding chip according to claim 2 to identify a DNA fingerprint of a rice germplasm resource, wherein the method comprises:
   (1) extracting genomic DNA from a rice germ plasma resource;
   (2) applying the extracted genomic DNA to the chip;
   (3) detecting hybridization between the extracted genomic DNA and the nucleotide sequences on the chip to produce genotyping data;
   (4) analyzing the genotyping data; and
   (5) identifying the DNA fingerprint of the rice germplasm resource based on the genotyping data.

4. A method comprising using the rice whole genome breeding chip according to claim 2 to identify a genotype of a rice hybrid progeny, wherein the method comprises:
   (1) extracting genomic DNA from a sample obtained from a rice hybrid progeny;
   (2) applying the extracted genomic DNA to the chip;
   (3) detecting hybridization between the extracted genomic DNA and the nucleotide sequences on the chip to produce genotyping data;
   (4) analyzing the genotyping data; and (5) identifying the genotype of the rice hybrid progeny based on the genotyping data.

5. A method comprising using the rice whole genome breeding chip according to claim 2 to identify a rice variety, wherein the method comprises:
(1) extracting genomic DNA from a rice sample;
(2) applying the extracted genomic DNA to the chip;
(3) detecting hybridization between the extracted genomic DNA and the nucleotide sequences on the chip to produce genotyping data;
(4) analyzing the genotyping data; and
(5) identifying the rice variety based on the genotyping data.

6. A method comprising using the rice whole genome breeding chip according to claim 2 to identify a genetic background of a rice breeding material, wherein the method comprises:
(1) extracting genomic DNA from a rice breeding material;
(2) applying the extracted genomic DNA to the chip;
(3) detecting hybridization between the extracted genomic DNA and the nucleotide sequences on the chip to produce genotyping data;
(4) analyzing the genotyping data; and
(5) identifying the genetic background of the rice breeding material based on the genotyping data.

7. A method comprising using the rice whole genome breeding chip according to claim 2 to perform a rice genome-wide association study, wherein the method comprises:
(1) extracting genomic DNA from rice samples having a specific trait;
(2) applying the extracted genomic DNA to the chip;
(3) detecting hybridization between the extracted genomic DNA and the nucleotide sequences on the chip to produce genotyping data; and
(4) analyzing the genotyping data to detect an association between the genotype of the samples and the specific trait, thereby performing a genome wide association study.

* * * * *